(12) United States Patent
Dadd et al.

(10) Patent No.: US 7,269,461 B2
(45) Date of Patent: *Sep. 11, 2007

(54) DOUBLE STYLET INSERTION TOOL FOR A COCHLEAR IMPLANT ELECTRODE ARRAY

(75) Inventors: Fysh Dadd, Lane Cove (AU); Derek Ian Darley, Cromer Heights (AU); Peter Gibson, South Coogee (AU); John L. Parker, Roseville (AU); Claudiu Treaba, Wollstonecraft (AU)

(73) Assignee: Cochlear Limited, Lane Cove, NSW (AU)

( * ) Notice: Subject to any disclaimer, the term of this patent is extended or adjusted under 35 U.S.C. 154(b) by 685 days.

This patent is subject to a terminal disclaimer.

(21) Appl. No.: 10/070,102

(22) PCT Filed: Sep. 28, 2001

(86) PCT No.: PCT/AU01/01230

§ 371 (c)(1),
(2), (4) Date: Jul. 8, 2002

(87) PCT Pub. No.: WO02/30507

PCT Pub. Date: Apr. 18, 2002

(65) Prior Publication Data

US 2003/0045921 A1    Mar. 6, 2003

(30) Foreign Application Priority Data

Oct. 11, 2000 (AU) .................... PR 0684
Oct. 17, 2000 (AU) .................... PR 0807
Oct. 25, 2000 (AU) .................... PR 1005
Nov. 29, 2000 (AU) .................... PR 1778

(51) Int. Cl.
*A61N 1/05* (2006.01)

(52) U.S. Cl. .................... 607/137; 607/55; 607/56; 607/57

(58) Field of Classification Search ........ 607/136–137, 607/55–57, 115–116, 125–126; 600/379
See application file for complete search history.

(56) References Cited

U.S. PATENT DOCUMENTS 3,890,977 A    6/1975    Wilson (Continued)

FOREIGN PATENT DOCUMENTS

EP    0002 068    11/1978

(Continued)

OTHER PUBLICATIONS

European Supplementary Search Report, dated Jan. 22, 2004; corresponding application No. 01973835.0-2305; applicant Cochlear Limited.

(Continued)

*Primary Examiner*—Carl Layno
*Assistant Examiner*—Jessica L. Reidel
(74) *Attorney, Agent, or Firm*—Connolly Bove Lodge & Hutz LLP (57) ABSTRACT

A cochlear implant electrode assembly device (10) comprising an elongate electrode carrier member (11), a first stiffening element (15a), and a second stiffening element (15b). The carrier member (11) is made of a resiliently flexible first material and has a plurality of electrodes (12) mounted thereon. The carrier member (11) has a first configuration selected to allow it to be inserted into an implantee's cochlea (30), a second configuration wherein it is curved in shape to match a surface of the cochlea (30), and at least one intermediate configuration between the first and second configurations. Both the first and second stiffening elements (15a, 15b) are made of a material relatively stiffer than said the material and in combination bias the elongate member into the first configuration. If either the first stiffening element (15a) or the second stiffening element (15b) are removed, the elongate member (11) adopts the at least one intermediate configuration.

28 Claims, 2 Drawing Sheets

U.S. PATENT DOCUMENTS

| | | | |
|---|---|---|---|
| 4,046,151 A * | 9/1977 | Rose | 607/127 |
| 4,154,247 A * | 5/1979 | O'Neill | 607/125 |
| 4,357,497 A | 11/1982 | Hochmair et al. | |
| 4,381,013 A * | 4/1983 | Dutcher | 607/127 |
| 4,532,930 A | 8/1985 | Crosby et al. | |
| 4,762,135 A | 8/1988 | van der Puije et al. | |
| 5,645,585 A | 7/1997 | Kuzma | |
| 5,653,742 A * | 8/1997 | Parker et al. | 607/137 |
| 5,755,765 A | 5/1998 | Hyde et al. | |
| 5,769,077 A | 6/1998 | Lindegren | |
| 5,782,744 A | 7/1998 | Money | |
| 5,902,329 A | 5/1999 | Hoffmann et al. | |
| 6,038,484 A * | 3/2000 | Kuzma | 607/137 |
| 6,119,044 A * | 9/2000 | Kuzma | 607/137 |
| 6,304,787 B1 | 10/2001 | Kuzma et al. | |
| 6,309,410 B1 | 10/2001 | Kuzma et al. | |
| 6,421,569 B1 * | 7/2002 | Treaba et al. | 607/137 |
| 2003/0045921 A1 | 3/2003 | Dadd et al. | |
| 2003/0181967 A1 * | 9/2003 | Dadd et al. | 607/122 |
| 2004/0030376 A1 | 2/2004 | Gibson et al. | |
| 2004/0078057 A1 | 4/2004 | Gibson | |
| 2004/0116995 A1 | 6/2004 | Dadd | |
| 2004/0122501 A1 | 6/2004 | Dadd et al. | |

FOREIGN PATENT DOCUMENTS

| | | |
|---|---|---|
| EP | 0350 188 A1 | 6/1989 |
| EP | 0 602 859 A2 | 6/1994 |
| EP | 0653223 A2 | 5/1995 |
| EP | 0 739 642 A2 | 10/1996 |
| EP | 0773037 A2 | 5/1997 |
| EP | 0 778 043 A1 | 6/1997 |
| EP | 0 778 044 A2 | 6/1997 |
| EP | 0 778 044 A3 | 7/1997 |
| EP | 0 783 900 A2 | 7/1997 |
| EP | 0 783 901 A2 | 7/1997 |
| EP | 0 784 994 A1 | 7/1997 |
| EP | 0784 995 A1 | 7/1997 |
| EP | 0 919 254 A2 | 6/1999 |
| GB | 2 217 993 A | 11/1989 |
| WO | WO97/10784 A1 | 3/1997 |

OTHER PUBLICATIONS

Research Disclosure; Nov. 1997; No. 403-40349, 790-791pp; "Epicardial-Transvenous Left Ventricular Lead with Dual Ring Electrodes (Cathode Ring & Anode Ring) Design"; by Disclosed Anonvmouslv; K. Mason Publications Ltd England.

Research Disclosure; Nov. 1997; No. 403-40342, 785pp; "Epicardial-Transvenous Left Atrial Lead with Wound 'Butterfly Tongue' Electrode"; by Disclosed Anonymously; K Mason Publications Ltd-England.

Australian International-Type Search Report dated Dec. 15, 2000; priority National Application No. PR 0684; Applicant: Cochlear Limited.

Australian International-Type Search Report dated Dec. 15, 2000; priority National Application No. PR 0807; Applicant; Cochlear Limited.

Australian International-Type Search Report dated Dec. 15, 2000; priority National Application No. PR 1005; Applicant: Cochlear Limited.

PCT International Search Report; PCT/AU01/01230;—filed Sep. 28, 2001;—Applicant: Cochlear Limited.

PCT International Preliminary Examination Report; PCT/AU01/01230; filed Sep. 28, 2001;—Applicant: Cochlear Limited.

International Search Report for PCT/AU01/01232, dated Oct. 26, 2001.

International Preliminary Examination Report, for PCT/AU01/01232 dated Feb. 25, 2002.

Australian Patent Office International-Type-Search Report, PR 0541 dated Dec. 20, 2000.

Australian Patent Office International-Type-Search Report, PR 0542, dated Dec. 20, 2000.

International Search Report for PCT/AU01/01231, dated Oct. 26, 2001.

* cited by examiner

DOUBLE STYLET INSERTION TOOL FOR A COCHLEAR IMPLANT ELECTRODE ARRAY

FIELD OF THE INVENTION

The present invention relates to an implantable device and, in particular, to an implantable cochlear electrode assembly.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two key components, namely an external component commonly referred to as a processor unit, and an implanted internal component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit typically included the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

The external componentry of the cochlear implant has been traditionally carried on the body of the implantee, such as in a pocket of the implantee's clothing, a belt pouch or in a harness, while the microphone has been mounted on a clip mounted behind the ear or on a clothing lapel of the implantee.

More recently, due in the main to improvements in technology, the physical dimensions of the speech processor have been able to be reduced allowing for the external componentry to be housed in a small unit capable of being worn behind the ear of the implantee. This unit has allowed the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

Together with improvements in available technology much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea-stimulating signal within a preselected frequency range to the appropriate cochlea region. The electrical currents and electric fields from each electrode stimulate the cilia disposed on the modiola of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the shape of the modiola and must also be shaped such that the insertion process causes minimal trauma to the sensitive structures of the cochlea. In this sense it has been found to be desirable for the electrode array be generally straight during the insertion procedure.

Several procedures have been adopted to provide an electrode assembly that is relatively straightforward to insert while adopting a curved configuration following insertion in the cochlea. In one case, a platinum wire stylet is used to hold a pre-curved electrode array in a generally straight configuration up until insertion. Following insertion, the platinum stylet is withdrawn allowing the array to return to its pre-curved configuration.

In another development, a bimetallic filament (such as nickel/titanium) or a shape memory alloy (eg. an alloy of nickel and titanium) is positioned in the electrode assembly and used to again hold a pre-curved electrode array in a generally straight configuration while the array is at about room temperature. On insertion into the body and exposure to body temperature, the filament or alloy bends into a pre-selected curved configuration.

In a still further arrangement, a longitudinal element that is arranged on one side of the array and constructed to change its dimension on insertion can be utilised. For example, the longitudinal element could include a hydrogel, such as polyacrylic acid (PAA) or polyvinyl alcohol (PVA), which expands after insertion by absorbing water from the cochlear fluid.

In developing such electrode array designs, it is of great importance that the design be constructed to minimise potential damage to sensitive structures in the cochlear on insertion and placement. Each of the above constructions suffer from a number of disadvantages in this regard.

Still further, it has been proposed to straighten pre-curved electrode arrays using inserted longitudinal elements or surrounding sheaths formed from bioresorbable materials that dissolve or soften on implantation. A disadvantage with use of such bioresorbable materials is that, due to the generally wet nature of the surgical environment, the polymer can dissolve or soften before the electrode array is appropriately positioned.

The present invention is directed to an electrode assembly adapted to overcome some of the difficulties of prior art electrode assemblies.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an implantable tissue-stimulating device comprising:

an elongate member having a plurality of electrodes mounted thereon and having a first configuration selected to allow said member to be inserted into an implantee's body, a second configuration wherein said elongate member is adapted to apply a preselected tissue stimulation with the electrodes, and at least one intermediate configuration between said first and second configurations, said elongate member being made of a resiliently flexible first material:
  a first stiffening element; and
  a second stiffening element;
  wherein said first stiffening element and said second stiffening element in combination bias said elongate member into said first configuration and further wherein if either the first stiffening element or the second stiffening element is removed, the elongate member adopts said at least one intermediate configuration.

In a preferred embodiment, the second configuration of the elongate member is curved. More preferably, the elongate member adopts a spiral configuration when in the second configuration.

According to a second aspect, the present invention is a cochlear implant electrode assembly device comprising:

an elongate electrode carrier member having a plurality of electrodes mounted thereon and having a first configuration selected to allow said member to be inserted into an implantee's cochlea, a second configuration wherein said elongate member is curved to match a surface of said cochlea, and at least one intermediate configuration between said first and second configurations, said elongate member being made of a resiliently flexible first material:
  a first stiffening element; and
  a second stiffening element;
  wherein said first stiffening element and said second stiffening element in combination bias said elongate member into said first configuration and further wherein if either the first stiffening element or the second stiffening element is removed, the elongate member adopts said at least one intermediate configuration.

The elongate member is preferably preformed from a plastics material with memory and is preformed to the second configuration. The elongate member preferably has a first end that is firstly inserted into the implantee.

In a further embodiment, the elongate member can have a resiliently flexible tip member extending forwardly from the first end of the body. The tip member preferably has a distal end and a proximal end. The tip member can have a stiffness that is relatively less stiff than said stiffening element. The tip member can further be formed of a material that is substantially the same or the same stiffness as the body of the elongate member. In another embodiment, the tip member can be formed of a material that is relatively less stiff than at least a portion of the elongate member. In a further embodiment, the tip member can be formed of a material that undergoes a change in stiffness, preferably a decrease in stiffness, on insertion into the body, such as the cochlea.

In a further embodiment, the stiffness of the tip member can vary along at least a portion of its length from its distal end to its proximal end. In one embodiment, the stiffness of the tip member can vary over the entire length of the tip member or only a portion thereof. The stiffness can increase from the distal end to the proximal end. In one embodiment, the stiffness of the tip member over said portion or its length can increase gradually from its distal end towards to the proximal end. The increase in stiffness can be substantially smooth or increase in a stepwise fashion.

In a further embodiment, the tip member can be formed of the same material as the body of the elongate member. In another embodiment, the tip member can be formed of a different material to that of the body of the elongate member. The tip member can be comprised of an inner relatively stiff core of material having a tapered end, with at least the tapered end being overlaid by a relatively flexible material that extends beyond the tapered end of the core material so that the tip member undergoes a gradual decrease in flexibility in the region of the tapered end of the core moving away from the distal end.

The tip member can be formed separately to the body of the elongate member and mounted thereto. For example, the tip member can be adhered to the first end of the body of the elongate member. In another embodiment, the tip member can be integrally formed with the body of the elongate member. The tip member can be formed from a silicone material. In another embodiment, the tip member can be formed of an elastomeric material, such as polyurethane.

In another embodiment, the tip member can have a plurality of metallic particles dispersed therethrough. The metallic particles can be substantially evenly dispersed through the tip member. Alternatively, the metallic particles can be non-evenly dispersed throughout the tip member. In one embodiment, the metallic particles can increase in density away from the distal end towards the proximal end of the tip member. By varying the density of the metallic particles, it is possible to vary the relative stiffness of the tip member.

The metallic particles preferably comprise a biocompatible material, such as platinum. The particles can be substantially spherical or spherical. It will be appreciated that the particles can have other suitable shapes. In one embodiment, the particles can have a diameter between about 50 μm and 100 μm.

In addition to, or instead of, being used to potentially modify the physical characteristics of the tip member, the provision of the metallic particles also result in the tip member being detectable by fluoroscopy and X-ray techniques. This provides another means for the surgeon to monitor the placement and position of the tip member during or after insertion of the electrode array in the body, such as in the cochlea.

When the elongate member is in the first configuration, the tip member is preferably substantially straight and, more preferably, straight.

In a further embodiment, the tip member can be coated with a lubricious material. The lubricious material can be a bioresorbable or non-bioresorbable material.

The tip member can be formed from, or incorporate as a portion thereof, a bioresorbable material. The presence of the bioresorbable material preferably results in the flexibility of the tip member increasing on insertion of the tip member into the body, such as the cochlea. The bioresorbable material in the tip member can be selected from the group consisting of polyacrylic acid (PAA), polyvinyl alcohol (PVA), polylactic acid (PLA) and polyglycolic acid (PGA).

In another embodiment, the tip member can be formed from, or incorporate as a portion thereof, a polymeric coating which becomes softer, and so increases in resilient flexibility, in the presence of moisture or body heat.

The tip member preferably has a length from its distal end to its proximal end in the range of about 0.3 to 4 mm, more preferably about 1.0 to 3 mm. The diameter of the tip member can be substantially constant for a majority of its length or can vary in diameter. The tip member can be substantially cylindrical, cylindrical, or non-cylindrical for a majority of its length. At the distal end, the diameter preferably gradually decreases to form a rounded end. The maximum diameter of the tip member is preferably about 0.55 mm.

In one embodiment, the tip member can be solid. In another embodiment, the tip member can have an external wall defining a cavity. In one embodiment, the cavity can have a diameter greater than that of the receiving portion of the body of the elongate member. In a further embodiment, the cavity can extend from the proximal end towards the distal end of the tip member. The cavity can decrease in diameter away from the proximal end. The cavity can be in communication with a distal end of the receiving portion of the body of the elongate member. In a further embodiment, the stiffening means can extend into the cavity when positioned within the device or assembly according to the respective aspects of the present invention. In a preferred embodiment, the tip member can move relative to the stiffening means when it extends into the cavity of the tip member.

In general, the tip could be made of a combination of materials arranged in a variety of geometries depending on the specific design goal. The outside shape and size of the tip can also be made in a variety of forms depending on the design goal.

In a preferred embodiment, the first configuration is preferably substantially straight. More preferably, the first configuration is straight.

In a preferred embodiment, the elongate member is formed from a suitable biocompatible material. In one embodiment, the material can be a silicone, such as a flexible silicone elastomer Silastic. Silastic MDX 4-4210 is an example of one suitable silicone for use in the formation of the elongate member. In another embodiment, the elongate member can be formed from a polyurethane or other similar materials.

In one embodiment, the first and second stiffening elements can be formed of the same material.

In one embodiment, the first stiffening element is made of a material that is relatively stiffer than the first material. In another embodiment, the second stiffening element can be relatively stiffer than said first stiffening element. In another embodiment, the second stiffening element can be relatively less stiff than the first stiffening element. In a still further embodiment, the first and second stiffening element can have the same stiffness.

Where the second stiffening element is relatively stiffer than the first stiffening element, the relatively greater stiffness of the second stiffening element can be provided by its structural parameters. For example, the second stiffening element can have a greater diameter than the first stiffening element.

The first stiffening element and/or the second stiffening element can be formed of a bioresorbable material which dissolves or softens on exposure to a fluid. The stiffening elements can dissolve or soften on exposure to a saline solution or a body fluid of the implantee such as cochlear fluid.

In a further embodiment, the bioresorbable material used for each stiffening element can be selected from the group comprising polyacrylic acid (PAA), polyvinyl alcohol (PVA), polylactic acid (PLA) and polyglycolic acid (PGA).

In another embodiment, the first and/or second stiffening element can be formed from a non-bioresorbable material. In this embodiment, the first and/or second stiffening element can comprise a metallic or plastic stylet. The stylets can extend through a single lumen in the elongate member or through respective lumens in the elongate member. The respective stylets can be positioned side-by-side in the elongate member. In another embodiment, one of said stylets can extend through a lumen of another tubular stylet. For example, the second stylet may extend through a lumen of the first tubular stylet. The first tubular stylet can be cylindrical or have another cross-sectional shape.

In one embodiment, each stylet can be formed from a biocompatible material, such as a metal or metallic alloy. In a preferred embodiment, each metal stylet can be formed from platinum.

In a still further embodiment, the first and/or second stiffening element can be formed from a shape memory alloy or a heat sensitive material. For example, each stiffening element can be formed from an alloy of nickel and titanium, or a bimetallic element formed from two layers of different metals, that is shaped to take a straight or substantially straight configuration at room temperature but bend into another shape once it is exposed to body temperature.

In yet another embodiment, the first and second stiffening elements can be of different lengths. For example, it may be desirable for the relatively stiffer stylet to have a shorter length and the relatively more flexible stylet to have a longer length, or vice versa. It is also envisaged that each stylet can have the same length.

In one embodiment, the lumen for the stylet can be cylindrical and also can have an opening formed therein. In the case where one or two metal stylets are used, the stylet or stylets can extend out of the opening allowing the stylet or stylets to be manipulated and removed from the lumen during or following insertion of the device.

In the case where the first and/or second stiffening elements are formed of a bioresorbable material, the opening can act as a fluid ingress means allowing body fluids to enter the lumen on insertion of the device into an implantee.

Where the first stiffening element is a metallic or metallic alloy stylet, the second stiffening element can be formed of a bioresorbable material which dissolves or softens on exposure to a fluid, or vice versa. The bioresorbable material can dissolve or soften on exposure to a saline solution or a body fluid of the implantee, such as cochlear fluid.

In a further embodiment, the bioresorbable material is selected from the group comprising polyacrylic acid (PAA), polyvinyl alcohol (PVA), polylactic acid (PLA) and polyglycolic acid (PGA).

The device can include an additional layer surrounding the elongate member. The additional layer can have a first rate of fluid ingress therethrough and have at least one fluid ingress means formed therein, the rate of fluid ingress through the fluid ingress means being greater than the first rate of fluid ingress through the additional layer.

The fluid ingress means can comprise one or more openings in the additional layer. The openings can be closable. The openings can comprise slits in the additional layer. The slits can be formed to allow substantially the same or the same rate of ingress of fluid through the additional layer. In another embodiment, at least one slit can allow a different rate of progress of fluid through the additional layer compared to the other slits.

Where the first stiffening element is a metal or bioresorbable stylet, the second stiffening element can, in one embodiment, be formed from a shape memory or heat sensitive material, or vice versa. For example, the second stiffening element can be formed from a shape memory alloy or a bimetallic filament (such as nickel and titanium alloy or a bimetallic filament comprising respective layers of such metals) that is shaped to maintain the straight or substantially straight configuration of the elongate member at room temperature but will bend into another shape once exposed to body temperature.

Preferably, while both the first and second stiffening elements are in position within the device, it will retain the first configuration, which as discussed is preferably straight. If the first stiffening element is removed, whether it is by physical removal or otherwise, the remaining second stiffening element preferably has insufficient strength to retain the elongate member in its first configuration. It is preferred that the elongate member, on removal of the first stiffening element, will adopt an intermediate configuration in which the elongate member has at least some curvature. On subsequent removal of the second stiffening element, the elongate member is free to adopt the fully curved second configuration desired of an implant after insertion into the cochlea.

The present invention provides a surgeon with a means to at least partially control the rate of curvature formation in a cochlear electrode assembly during insertion into the cochlea. Such increased control is envisaged to reduce the potential for trauma to the cochlea caused by electrode assembly insertion.

In a further embodiment, at least a portion of an outer surface of the elongate member can have a coating of a lubricious material. In one embodiment, a substantial portion or the entire outer surface of the elongate member can have a coating of the lubricious material.

In this embodiment, the lubricious material can be selected from the group comprising polyacrylic acid (PAA), polyvinyl alcohol (PVA), polylactic acid (PLA) and polyglycolic acid (PGA). It is envisaged that other similar materials could also be used.

According to a third aspect, the present invention is a cochlear implant electrode assembly device comprising:

an elongate electrode carrier member having a plurality of electrodes mounted thereon and having a first configuration selected to allow said member to be inserted into an implantee's cochlea, a second configuration wherein said elongate member is curved to match a surface of said cochlea, and at least one intermediate configuration between said first and second configurations, said elongate member being made of a resiliently flexible first material;

a first stiffening element made of a material relatively stiffer than said first material; and a second stiffening element that is relatively stiffer than said first stiffening element;

wherein said first stiffening element and said second stiffening element in combination bias said elongate member into said first configuration and further wherein if either the first stiffening element or the second stiffening element is removed, the elongate member adopts said at least one intermediate configuration.

In a further embodiment, the device can have one or more of the preferred features of the first and second aspects.

In a further aspect, the present invention comprises a method of implanting a tissue-stimulating device or cochlear electrode assembly device as defined herein in a body of an implantee.

In this aspect, the method can comprise a step of accessing the implantation site and then a step of inserting the device. Prior to insertion, the device is preferably substantially straight or straight. On insertion, the device can adopt an intermediate configuration (as defined herein). Either prior to full insertion or following full insertion, the device preferably adopts its second configuration.

Once implanted, the electrodes can receive stimulation signals from a stimulator means. The stimulator means is preferably electrically connected to the elongate member by way of an electrical lead. The lead can include the one or more wires extending from each electrode of the array mounted on the elongate member.

In one embodiment, the lead can extend from the elongate member to the stimulator means or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means.

The stimulator means is preferably positioned within a housing that is implantable within the implantee. The housing for the stimulator means is preferably implantable within the bony well in the bone behind the ear posterior to the mastoid.

When implantable, the housing preferably contains, in addition to the stimulator means, a receiver means. The receiver means is preferably adapted to receive signals from a controller means. The controller means is, in use, preferably mounted external to the body of the implantee such that the signals are transmitted transcutaneously through the implantee.

Signals can preferably travel from the controller means to the receiver means and vice versa. The receiver means can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms already developed for cochlear implant systems. The encoded sequence is transferred to the implanted stimulator/receiver means using the transmitter and receiver coils. The implanted stimulator/receiver means demodulates the FM signals and allocates the electrical pulses to the appropriate attached electrode by an algorithm which is consistent with the chosen speech coding strategy.

The external controller further comprises a power supply. The power supply can comprise one or more rechargeable batteries. The transmitter and receiver coils are used to provide power via transcutaneous induction to the implanted stimulator/receiver means and the electrode array.

While the implant system can rely on external componentry, in another embodiment, the controller means, including the microphone, speech processor and power supply can also be implantable. In this embodiment, the controller means can be contained within a hermetically sealed housing or the housing used for the stimulator means.

BRIEF DESCRIPTION OF THE DRAWINGS

By way of example only, preferred embodiments of the invention are now described with reference to the accompanying drawings, in which.

PREFERRED MODE OF CARRYING OUT THE INVENTION

One embodiment of a cochlear implant electrode assembly according to the present invention is depicted generally as 10 in the drawings.

Figure 1:
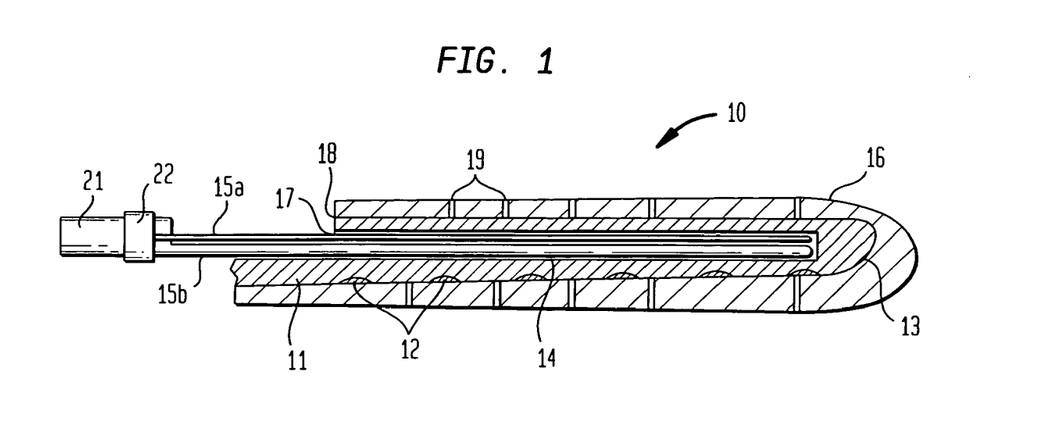
FIG. 1 is a simplified cross-sectional view of one embodiment of an electrode assembly according to the present invention depicted in its first configuration.
Figure 2:
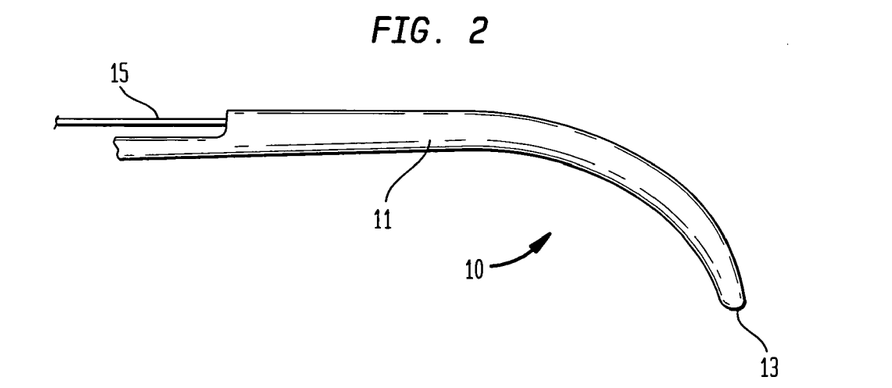
FIG. 2 is a simplified side elevational view of the electrode assembly of FIG. 1 depicted in an intermediate configuration.
Figure 3:
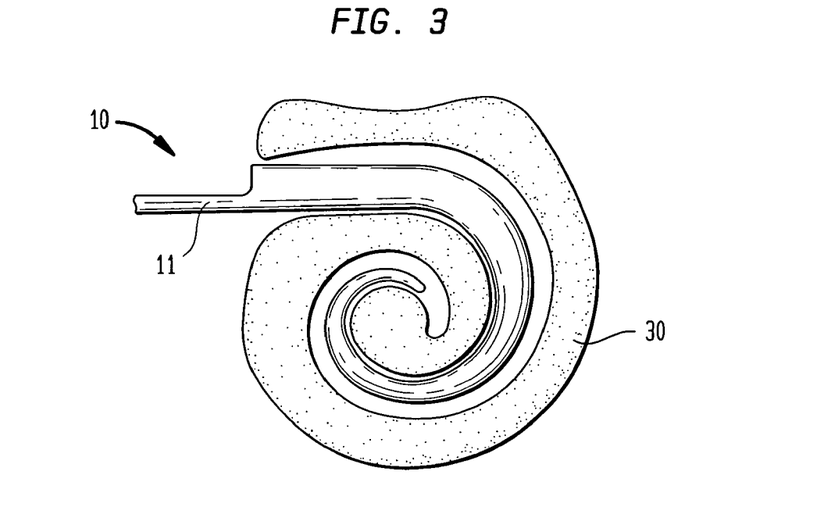
FIG. 3 is a simplified side elevational view of the electrode assembly depicted in its second configuration.

The depicted electrode assembly 10 has an electrical lead extending back to a stimulator/receiver housing. In considering this invention, it is to be understood that each electrode may have one or more wires (not depicted) electrically connected thereto and extending from each respective electrode back through the lead to the stimulator/receiver. The assembly 10 comprises an elongate electrode carrier member 11 having a plurality of electrodes 12 mounted thereon. For the purposes of clarity, the electrodes 12 depicted in FIG. 1 are not necessarily shown to scale. The electrodes 12 are not depicted in FIGS. 2 and 3 for reasons of clarity. As depicted in FIG. 1, the carrier member 11 can have an additional layer 16 surrounding 16 the carrier member 11. The additional layer surrounding the carrier member 16 may include fluid ingress means 19.

The depicted elongate member 11 is preformed from a resiliently flexible silicone with memory and is preformed to a curved configuration suitable for insertion in the scala tympani of the cochlea. The elongate member 11 has a first end 13 that is firstly inserted into the implantee on insertion of the assembly 10.

Figures 4, 5A:
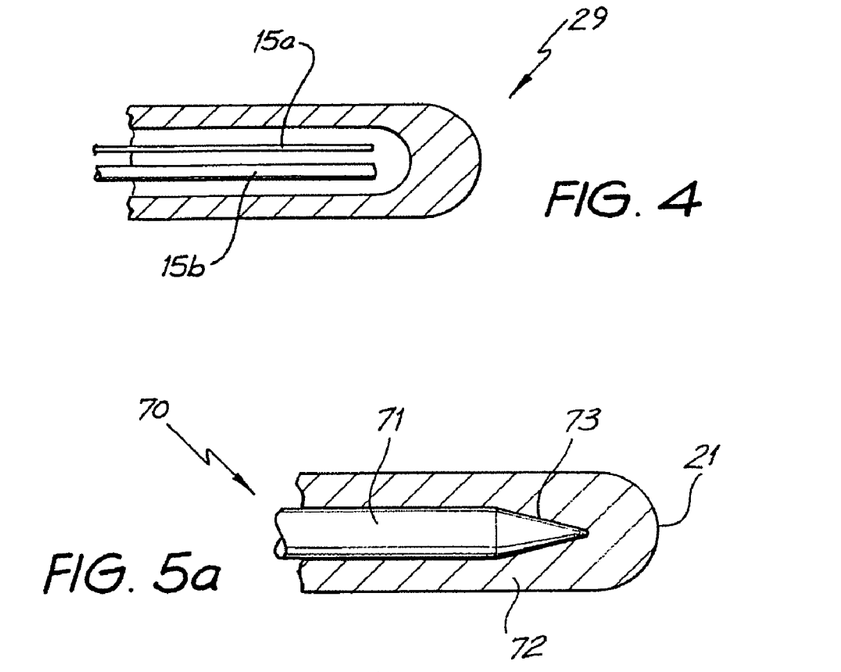
FIGS. 4 and 5a-5d depict alternative tip structures for the electrode assembly depicted in FIG. 1.

As depicted in FIG. 4. the elongate member 11 can have a tip member 29 integrally formed with its first end 13. The tip 29 is formed from the same silicone used to fabricate the elongate member 11 and, in the depicted embodiment, the material of tip member 29 has a resilient flexibility equal to that of the material used for the carrier member 11, Possible alternative constructions for the tip member 29 are provided in FIGS. 5a-5d. As depicted in FIG. 5a, the tip member 70 can be solid and formed of an inner core 71 of relatively stiff material 71 and an outer layer 72 of relatively flexible material. The core 71 can taper in diameter over region 73 towards the distal end 21. The taper 73 causes the overall stiffness of the tip 70 to increase over the length of the taper 73 away from the distal end 21. The outer layer 72 can be formed of the same material as the remainder of the body of the elongate carrier member 11 or can be a different material.

Figure 5B:
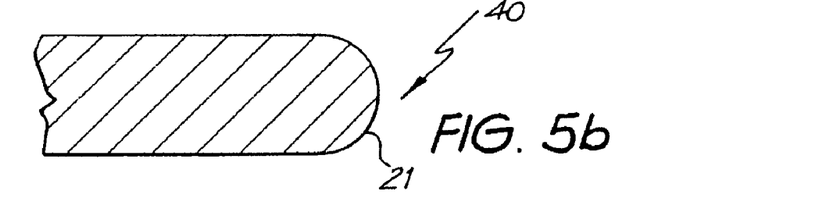

As depicted in FIG. 5b, the tip member 40 can comprise a solid mass integrally formed to the first end 13 of the elongate carrier 11.

Figure 5C:
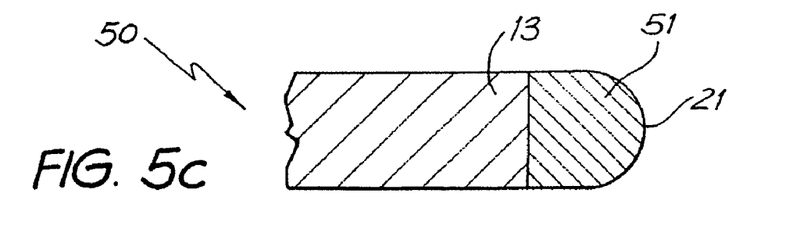

Still further and as depicted in FIG. 5c, the tip member 50 can comprise a solid mass 51 that is formed separately from the carrier member 11 and subsequently adhered thereto.

Figure 5D:
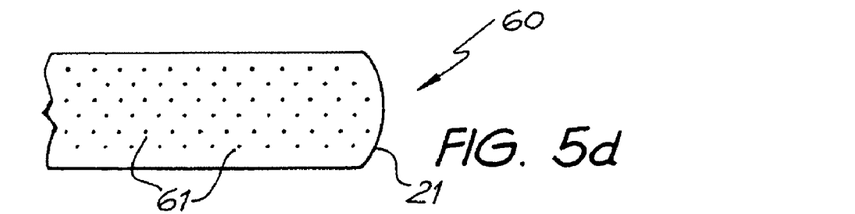

As depicted in FIG. 5d, the tip member 60 can comprise an elastomeric silicone material having a plurality of substantially spherical platinum particles 61 dispersed therethrough. The particles 61 have a diameter between about 50 μm and 100 μm. It will be appreciated that the particles 61 depicted in FIG. 5d are not drawn to scale.

In FIG. 5d. the particles 61 are depicted as substantially evenly dispersed through the tip member 60. In another embodiment, the particles could be non-evenly dispersed through the tip member. For example, the particles could increase in density away from the distal end 21 towards the proximal end of the tip member 60. By varying the density of the platinum particles 61, it is possible to vary the relative stiffness of the tip member 60.

In addition to, or instead of, being used to potentially modify the physical characteristics of the tip member, the provision of the metallic particles 61 also result in the tip member 60 being detectable by fluoroscopy and X-ray techniques. This provides another means for the surgeon to either monitor the placement and position of the tip member 60 during or after insertion of the electrode array 10 in an implantee's cochlea.

Disposed within a substantially cylindrical lumen 14 is a substantially straight first platinum stylet 15a and a second substantially straight platinum stylet 15b. The stylet 15a is relatively stiffer than the elongate carrier 11 but alone has a stiffness that is insufficient to retain the silicone elongate member 11 in the straight configuration depicted in FIG. 1. The second stylet 15b has a greater diameter than stylet 15a and is relatively stiffer than stylet 15a. Stylet 15b extends through opening 17 in lumen 14 to a handle 21 that can be gripped by the surgeon. Stylet 15a also extends out of opening 17 to a separate handle 22 mounted around and movable relative to handle 21. It should be noted that the stylets do not have to be the same length. It may be desirable to have a short relatively stiffer stylet and a long relatively more flexible stylet.

While stylets 15a, 15b are each depicted as a platinum stylet, one of both stiffening elements could be provided by a bioresorbable stylet formed from a bioresorbable polyacrylic acid (PAA) that is adapted to dissolve or soften on exposure to cochlear fluids. It will be appreciated that a bioresorbable stylet could be formed from other suitable bioresorbable materials. A stylet made from a shape memory or heat sensitive material could also be utilised as stylet 15a and/or stylet 15b.

While the elongate member 11 is manufactured with a preformed curved configuration, the assembly 10 is typically delivered to a surgeon with the stylets 15a, 15b in place. The placement of both of the stylets 15a, 15b in the lumen 14 is sufficient to hold the elongate member 11 in the straight configuration depicted in FIG. 1.

On insertion of the device 10 into the scala tympani of the cochlea 30 and when the first end 13 reaches the back of the basal turn, the surgeon can grip handle 21 and withdraw the second relatively stiffer stylet 15b from the lumen 14. As the stylet 15b is withdrawn, the elongate member 11 commences to re-curl (see FIG. 2) as the stiffness of the stylet 15a is insufficient to hold the elongate member 11 straight.

As the elongate member 11 curls, the surgeon can continue to further insert the curled assembly 10 into the scala tympani until the desired insertion is attained. Upon desired insertion, the platinum stylet 15a can be fully withdrawn through the opening 17 of the lumen 14, using handle 22. On full withdrawal of the stylet 15a, the elongate member 11 is free to adopt the spiral configuration depicted in FIG. 3 with the electrodes 12 facing the modiola within the cochlea 30 so that they are positioned as close as possible to the spiral ganglia thereof. It is also envisaged that during this final insertion, the platinum stylet 15a can be simultaneously withdrawn using handle 22, through the opening 17 of the lumen 14 to further assist with the ease of insertion.

The combination of the first and second stiffening elements 15a, 15b provides the surgeon with greater control of the implantation procedure for the cochlear implant electrode assembly 10. The provision of greater control minimises the potential for trauma to the sensitive tissues inside the cochlea and also enhances the likelihood of successful placement of the assembly 10 at the first attempt.

While the preferred embodiment of the invention has been described in conjunction with a cochlear implant, it is to be understood that the present invention has wider application to other implantable electrodes, such as electrodes used with pacemakers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A cochlear implant electrode assembly device comprising:
    an elongate electrode carrier member having a plurality of electrodes mounted thereon and having a first substantially straight configuration selected to allow said member to be inserted into an implantee's cochlea, a second curved configuration wherein said elongate member is curved to match a surface of said cochlea, and at least one partially curved intermediate configuration between said first and second configurations, said elongate member being made of a resiliently flexible first material;
    a first stiffening element;
    and at least a second stiffening element;
    wherein said first stiffening element and said second stiffening element in combination bias said elongate member into said first configuration and further wherein if either the first stiffening element or the second stiffening element is removed from the elongate member, the elongate member adopts said at least one partially curved intermediate configuration.

2. A device of claim 1, wherein the elongate member adopts a spiral configuration when in the second configuration.

3. A device of claim 1, wherein the elongate member is preformed from a plastics material with memory and is preformed to the second configuration.

4. A device of claim 1, wherein the elongate member has a first end that is firstly inserted into the implantee.

5. A device of claim 4, wherein a resiliently flexible tip member extends forwardly from the first end of the elongate member.

6. A device of claim 5, wherein the tip member has a plurality of metallic particles dispersed therethrough.

7. A device of claim 1, wherein the elongate member is formed from a biocompatible material selected from the group comprising a silicone and a polyurethane.

8. A device of claim 1, wherein the first and second stiffening elements are formed of the same material.

9. A device of claim 1, wherein the first stiffening element is made of a material that is relatively stiffer than the first material.

10. A device of claim 9, wherein the second stiffening element is relatively stiffer than said first stiffening element.

11. A device of claim 10, wherein the second stiffening element has a greater diameter than the first stiffening element.

12. device of claim 1, wherein at least the first stiffening element is formed of a bioresorbable material which dissolves or softens on exposure to a fluid.

13. A device of claim 12, wherein the bioresorbable material of said at least first stiffening element is selected from the group comprising polyacrylic acid (PAA), polyvinyl alcohol (PVA), polylactic acid (PLA) and polyglycolic acid (PGA).

14. A device of claim 1, wherein at least the first stiffening element is formed from a non-bioresorbable material.

15. A device of claim 14, wherein at least the first stiffening element is a metallic or plastic stylet.

16. A device of claim 15, wherein the second stiffening element is a metallic or plastic stylet.

17. A device of claim 16, wherein the respective stylets extend through a single lumen in the elongate member.

18. A device of claim 16, wherein one of said stylets can extend through a lumen of the other stylet.

19. A. device of claim 1, wherein the first and/or second stiffening element are formed from a shape memory material.

20. A device of claim 1, wherein the first and second stiffening elements are of different lengths.

21. A device of claim 1, wherein the first stiffening element is a metallic or metallic alloy stylet, and the second stiffening element is formed of a bioresorbable material which dissolves or softens on exposure to a fluid.

22. A device of claim 21, wherein the bioresorbable material is selected from the group comprising polyacrylic acid (PAA), polyvinyl alcohol (PVA), polylactic acid (PLA) and polyglycolic acid (PGA).

23. A device of claim 1, wherein the device includes an additional layer surrounding the elongate member, the additional layer having a first rate of fluid ingress therethrough and have at least one fluid ingress means formed therein, the rate of fluid ingress through the fluid ingress means being greater than the first rate of fluid ingress through the additional layer.

24. A device of claim 23, wherein the fluid ingress means comprises one or more slits in the additional layer.

25. A device of claim 1, wherein the first stiffening element is a metal or bioresorbable stylet and the second stiffening element is formed from a shape memory material.

26. A device of claim 1, wherein at least a portion of an outer surface of the elongate member has a coating of a lubricious material.

27. A device of claim 26, wherein the lubricious material is selected from the group comprising polyacrylic acid (PAA), polyvinyl alcohol (PVA), polylactic acid (PLA) and polyglycolic acid (PGA).

28. A cochlear implant electrode assembly device comprising:
   an elongate electrode carrier member having a plurality of electrodes mounted thereon and having a first configuration selected to allow said member to be inserted into an implantee's cochlea, a second configuration wherein said elongate member is curved to match a surface of said cochlea, and at least one intermediate configuration between said first and second configurations, said elongate member being made of a resiliently flexible first material:
   a first stiffening element made of a material relatively stiffer than said first material; and
   a second stiffening element that is relatively stiffer than said first stiffening element;
   wherein said first stiffening element and said second stiffening element in combination bias said elongate member into said first configuration and further wherein if either the first stiffening element or the second stiffening element is removed from the elongate member, the elongate member adopts said at least one intermediate configuration.

* * * * *